United States Patent
Iwakiri et al.

(10) Patent No.: US 10,517,859 B2
(45) Date of Patent: Dec. 31, 2019

(54) GEL LOCAL ANESTHETIC AGENT AND GEL LOCAL ANESTHETIC PREPARATION USING SAME

(71) Applicant: TERUMO KABUSHIKI KAISHA, Tokyo (JP)

(72) Inventors: Chisato Iwakiri, Kanagawa (JP); Hideka Kikuchi, Kanagawa (JP); Koji Nakamura, Tokyo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/712,624

(22) Filed: Sep. 22, 2017

(65) Prior Publication Data

US 2018/0008586 A1    Jan. 11, 2018

Related U.S. Application Data

(63) Continuation of application No. PCT/JP2016/050355, filed on Jan. 7, 2016.

(30) Foreign Application Priority Data

Mar. 25, 2015   (JP) .................. 2015-063165

(51) Int. Cl.
 *A61K 31/445*  (2006.01)
 *A61K 45/06*   (2006.01)
 *A61K 31/704*  (2006.01)

(52) U.S. Cl.
 CPC .......... *A61K 31/445* (2013.01); *A61K 31/704* (2013.01); *A61K 45/06* (2013.01); *A61K 2300/00* (2013.01)

(58) Field of Classification Search
 CPC .... A61K 31/445; A61K 45/06; A61K 31/704; A61K 2300/00
 See application file for complete search history.

(56) References Cited

U.S. PATENT DOCUMENTS

| | | |
|---|---|---|
| 2006/0159632 A1 | 7/2006 | Ishibashi et al. |
| 2012/0004303 A1 | 1/2012 | Benson et al. |

FOREIGN PATENT DOCUMENTS

| | | |
|---|---|---|
| JP | 2004-196786 A | 7/2004 |
| JP | 2005-015479 A | 1/2005 |
| JP | 2006-160607 A | 6/2006 |
| JP | 2008-001688 A | 1/2008 |
| JP | 2011-508788 A | 3/2011 |
| JP | 5052558 B2 | 10/2012 |
| JP | 2013-523693 A | 6/2013 |
| JP | 2013-523694 A | 6/2013 |
| WO | WO-2009/129149 A2 | 10/2009 |
| WO | WO-2011/121074 A1 | 10/2011 |
| WO | WO-2011/121082 A2 | 10/2011 |
| WO | WO-2012/102210 A1 | 8/2012 |

OTHER PUBLICATIONS

Kano et al., "A comparative study of transdermal 10% lidocaine gel with and without glycyrrhetinic acid monohemiphthalate disodium for pain reduction at venous cannulation". Anesth. Analg. vol. 74, pp. 535-538, 1992 (Year: 1992).*

Mishima et al., "Promotion of nasal absorption of insulin by glycyrrhetinic acid derivatives. I". J. Pharmacobio-Dyn., vol. 12, pp. 31-36, 1989 (Year: 1989).*

Prescribing Information, Instillagel, Lidocaine and chlorhexidine Gel BP, 2012 (Year: 2012).*

International Search report issued in International Application No. PCT/JP2016/050355 dated Feb. 16, 2016.

Australian Office Action dated Mar. 22, 2018 in corresponding application No. 2016237984.

English Translation of the International Preliminary Report on Patentability dated Sep. 26, 2017 in corresponding application No. PCT/JP2016/050355.

Extended European Search Report dated Jul. 19, 2018 in corresponding application No. 16768089.

* cited by examiner

*Primary Examiner* — Barbara P Badio

(74) *Attorney, Agent, or Firm* — Foley & Lardner LLP

(57) ABSTRACT

A gel type local anesthetic agent of the present invention is a local anesthetic agent consisting of a local anesthetic having a tertiary amine and glycyrrhizic acid in which the local anesthetic and glycyrrhizic acid are gelated to form a gel type.

22 Claims, No Drawings

GEL LOCAL ANESTHETIC AGENT AND GEL LOCAL ANESTHETIC PREPARATION USING SAME

CROSS REFERENCE TO RELATED APPLICATIONS

The present application is a bypass continuation of PCT/JP2016/050355, filed on Jan. 7, 2016, which claims priority under 35 U.S.C. § 119(e) to JP 2015-063165, filed on Mar. 25, 2015, the contents of each of which are hereby incorporated by reference in their entireties.

TECHNICAL FIELD

The present invention relates to a gel type local anesthetic agent containing local anesthetic for local administration and a gel type local anesthetic preparation using it. The gel type local anesthetic agent is used for reducing pain in wound area, surgery area, or the like.

BACKGROUND ART

Local anesthetics are generally used for suppressing nociceptive pains and administered by local injection in general. The pharmaceutical composition for local injection generally contains a local anesthetic with concentration of 0.2 to 2%. In recent years, due to the reasons like a change in risk and benefit balance that is caused by standardization of anti-coagulation therapy after surgery or less invasive surgery, a situation has arrived in which epidural anesthesia, considered to be a gold standard up until now, cannot be the first choice for pain relief after surgery.

Opioid IV-PCA, peripheral nerve blocking, and combinations thereof are mainly used at present moment as a replacement method for epidural anesthesia. However, whereas the pain relieving effect after surgery is required for 1 to 3 days or so, the duration of effect of the peripheral nerve blocking based on injection of a local anesthetic is as short as a half day.

In recent years, a gelated local anesthetic agent containing local anesthetics has been suggested.

For example, disclosed in JP 2011-508788 W (Patent Literature 1) is a plurality of embedded type pharmaceutical depot preparation useful for alleviating, preventing, or treating pains and/or inflammations of a patient who is in need of the treatment in which the preparation contains at least one pharmaceutical depot preparation of a first set that can release, in an area under skin, a therapeutically effective bolus amount of pain reliever and/or anti-inflammation pharmaceutical, or pharmaceutically acceptable salts thereof, and at least one pharmaceutical depot preparation of a second set that can release for a period of at least 3 days a therapeutically effective amount of pain reliever and/or anti-inflammation pharmaceutical, or pharmaceutically acceptable salts thereof.

Furthermore, disclosed in JP 2013-523693 W (Patent Literature 2) is a thermally gelated and stabilized pharmaceutical composition of at least one local anesthetic, in which the composition has pH close to pKa of the local anesthetic and contains (a) base form of one or more kinds of local anesthetics (ATC code: NO1BB) of an amide type, (b) 10 to 30% by weight of polyoxyethylene castor oil, and (c) at least 15% by weight of one or more of surfactants for giving the thermal gelation property to the composition.

Furthermore, disclosed in JP 2013-523694 W (Patent Literature 3) is a stabilized and gelated aqueous bioadhesive pharmaceutical composition which contains (a) one or more kinds of local anesthetics in an anesthetically effective amount, (b) monoglyceride or diglyceride, or a mixture of long chain fatty acid thereof in an amount of 15 to 70% by weight, and (c) free long chain saturated or unsaturated fatty acid in an amount of 5 to 60% by weight, and has a behavior of an anisotropic organic phase which enables swelling in an administration area containing excessive moisture.

Furthermore, it has been found by the applicant of the present application that an aqueous solution containing glycyrrhizic acid at low concentration and a cationic substance can form a matrix (i.e., hydrogel), and suggested WO 2012/102210 A (Patent Literature 4) in which a gel composition containing a complex of (1) glycyrrhizic acid and a cationic substance is described.

CITATION LIST

Patent Literature

Patent Literature 1: JP 2011-508788 W
Patent Literature 2: JP 2013-523693 W
Patent Literature 3: JP 2013-523694 W
Patent Literature 4: WO 2012/102210 A

SUMMARY OF INVENTION

Technical Problem

Patent Literature 1 is useful in that a pain reliever and an anti-inflammatory agent can be released over a period of 3 days. However, according to Patent Literature 1, it is described that each pharmaceutical depot preparation of a first set and a second set contains at least one kind of a biodegradable polymer which contains one or more of poly(lactide-co-glycolide) (PLGA), polylactide (PLA), polyglycolide (PGA), D-lactide, D,L-lactide, L-lactide, D,L-lactide-ε-caprolactone, D,L-lactide-glycolide-ε-caprolactone, glycolide-caprolactone, poly(glycolide-co-caprolactone), and a combination thereof.

According to Patent Literature 2, polyoxyethylene castor oil and one or more kinds of a surfactant in an amount of 15% by weight or more for having thermal gelation property are included.

According to Patent Literature 3, monoglyceride or diglyceride, or a mixture of long chain fatty acid thereof, and free long chain saturated or unsaturated fatty acid are included.

The local anesthetic agent of each of the above patent literatures contains those other than local anesthetic due to formulation. Although they may not be harmful to a subject, they may cause a reduction in pharmaceutical effects of local anesthetic and a delayed healing of wound area or surgery area. Furthermore, although it is described in Patent Literature 4 that an aqueous solution containing glycyrrhizic acid at low concentration and a cationic substance can form a matrix (i.e., hydrogel), there is no disclosure regarding direct gelation of the local anesthetic.

Furthermore, because high pressure steam sterilization is necessary for use of the local anesthetic agent, it is required that the properties of the anesthetic agent (e.g., sustained release property) are not affected by it either before or after the sterilization.

An object of the present invention is to provide a gel type local anesthetic agent which does not require use of a compound for gelation of pharmaceuticals as the local anesthetic itself is gelated, shows no decrease in efficacy even after having high pressure steam sterilization, exhibits a sufficient analgesic effect at an early stage of administration, and has the analgesic effect maintained for a long period of time, and also to provide a gel type local anesthetic preparation using the gel type local anesthetic agent.

Solution to Problem

The above object is achieved by the following.

A local anesthetic agent consisting of a local anesthetic having a tertiary amine and glycyrrhizic acid in which the local anesthetic and glycyrrhizic acid are gelated to form a gel.

The above object is also achieved by the following.

A gel type local anesthetic preparation consisting of a container and the gel type local anesthetic agent encased in the container.

DESCRIPTION OF EMBODIMENTS

The gel type local anesthetic agent of the present invention is explained by using examples.

The gel type local anesthetic agent of the present invention is a local anesthetic agent consisting of a local anesthetic having a tertiary amine and glycyrrhizic acid in which the local anesthetic and glycyrrhizic acid are gelated to form a gel.

Glycyrrhizic acid is a substance which has a record of being used, as a pharmaceutical, for intravenous injection and is recognized with biocompatibility. As for the glycyrrhizic acid for use, glycyrrhizic acid or a water soluble salt thereof is suitable. Examples of the water soluble salt thereof include a potassium salt, an ammonium salt, and a sodium salt. In particular, an ammonium salt, which has a record of being used for intravenous injection, is preferable.

The gel type local anesthetic agent of the present invention forms a gel type anesthetic only with a local anesthetic and glycyrrhizic acid, which is a component that has been used on subjects.

According to the gel composition according to the present invention, a gel state is formed by a complex between glycyrrhizic acid and a local anesthetic having a tertiary amine. The term "gel" indicates a product in which a three-dimensional netlike structure is formed according to crosslinking among molecules and a solvent is absorbed within the structure to yield swelling. It is understood that, as an electrostatic interaction acting between the carboxy group of glycyrrhizic acid and a secondary or a tertiary amine of the local anesthetic occurs in the gel to form an ion complex, a fibrous molecular aggregate is formed by hydrogen bonding or hydrophobic interaction between the ion complexes, and a gel is generated as the aggregates entangle three-dimensionally with one another.

The local anesthetic to be used can be any kind as long as it has a local anesthetic activity and a tertiary amine. The local anesthetic can be any one of an amide type local anesthetic and an ester type local anesthetic.

Preferred examples of the local anesthetic include ropivacaine, bupivacaine, levobupivacaine, lidocaine, mepivacaine, dibucaine, and prilocaine, which are an amide type local anesthetic, and procaine, tetracaine, cocaine, chloroprocaine, and benzocaine, which are an ester type local anesthetic. Furthermore, it is preferable that the local anesthetic is at least one selected from those described above. As for the local anesthetic, ropivacaine is preferable due to having good property of forming a gel. Furthermore, two or more kinds of selected local anesthetic can be used selected from those described above.

It is also preferable that the local anesthetic to be used has plural amines. It is particularly preferable to have both of a secondary amine and a tertiary amine, or both of a primary amine and a tertiary amine. A good gel can be formed between them and glycyrrhizic acid. Furthermore, it is preferable that the amine of the local anesthetic is derived from a piperidine skeleton. It is particularly preferable that the local anesthetic to be used has both a secondary amine and a tertiary amine.

The local anesthetic agent preferably has pH of 6 or less. In particular, pH is preferably 5 or less, and more preferably 3.8 to 4.6.

Furthermore, the gel type local anesthetic agent of the present invention is treated by high pressure steam sterilization. By using high pressure steam sterilization, it becomes possible to provide the agent in pre-filled form (i.e., pre-filled preparation). Examples of the pre-filled form include syringe form (i.e., pre-filled syringe) and tube form.

Furthermore, according to the gel type local anesthetic agent of the present invention, it is preferable that the release rate of the local anesthetic is 20% or higher 1 hour after the administration, and release rate of the local anesthetic is lower than 80% 6 hours after the administration. As the numerical values of the release rate are within this range, not only the analgesic effect is exhibited at early stage like 1 hour after the administration of the gel type local anesthetic of the present invention but also the analgesic effect is maintained even after 6 hours. Furthermore, the release rate (%) is calculated as follows: (Amount of local anesthetic in released gel type local anesthetic agent/Total amount of local anesthetic in gel type local anesthetic agent×100). Furthermore, it is preferable that the release rate of the local anesthetic after 72 hours is 80% or higher. In particular, it is preferable that the release rate of the local anesthetic is 25% or higher 1 hour after the administration and also release rate of the local anesthetic is lower than 70% 6 hours after the administration. Furthermore, it is preferable that the release rate of the local anesthetic is 82% or higher 72 hours after the administration.

The gel type local anesthetic agent of the present invention is a hydrogel, and it can be prepared by mixing a homogeneous aqueous solution of glycyrrhizic acid with an aqueous solution of a local anesthetic having a tertiary amine.

For preparing a homogeneous aqueous solution of glycyrrhizic acid, both glycyrrhizic acid and a salt of glycyrrhizic acid can be used as glycyrrhizic acid. Examples of the salt of glycyrrhizic acid include a potassium salt, an ammonium salt, and a sodium salt. An ammonium salt is preferable among them.

The aqueous glycyrrhizic acid solution is a homogeneous aqueous solution of glycyrrhizic acid, and it preferably has concentration at which a gel is not generated by itself. The aqueous glycyrrhizic acid solution is preferably a solution with low viscosity. An aqueous glycyrrhizic acid solution with a concentration like 200 mg/mL or higher is known to form a gel by itself, for example. Furthermore, although an aqueous glycyrrhizic acid solution used as an injection solution for allergy and liver disorder has a concentration of 2 mg/mL and does not contain any gel, at high concentration, it is known to show weak self-crosslinking even in an acidic aqueous solution. It is noted in the interview form or the like of a glycyrrhizic acid preparation, that gelation may occur when the aqueous solution is acidified. Considering those facts and workability for solubilization in view of insolubility of glycyrrhizic acid in water, it is preferable that an aqueous solution of glycyrrhizic acid is generally prepared to have concentration of 200 mg/mL or less. Furthermore, because it is difficult to form a good gel at excessively low concentration, a concentration of 0.8 mg/mL or more is preferable.

It was found that, with regard to the ratio between glycyrrhizic acid and a local anesthetic having a tertiary amine in the gel type local anesthetic agent of the present invention, gel strength tends to be higher as the ratio of a local anesthetic having an amine increases. As such, the molar ratio ((b)/(a)) of (b) the local anesthetic having an amine relative to (a) glycyrrhizic acid is preferably 0.5 to 10, and particularly preferably 1 to 3. The amine of a local anesthetic may form an ion complex with glycyrrhizic acid.

Mixing of a homogeneous solution of glycyrrhizic acid with an aqueous solution of a local anesthetic having an anime can be carried out at 0 to 60° C., but it can be carried out at room temperature in general. Only by mixing those two liquids at room temperature can a gel be formed. The mixing is preferably carried out by adding an aqueous solution of a local anesthetic to an aqueous solution of glycyrrhizic acid. It is also possible that an aqueous solution of glycyrrhizic acid is added to an aqueous solution of a local anesthetic. In particular, it is preferable that mixing of the two, i.e., preparation of the gel type local anesthetic agent of the present invention, is carried out by preparing an aqueous solution of monoammonium glycyrrhizic acid and adding, in small portions, an aqueous solution of a local anesthetic thereto while stirring the aqueous solution of monoammonium glycyrrhizic acid. It is also possible that the gel type local anesthetic agent of the present invention is prepared without requiring any heating.

There is also a tendency that a harder gel is yielded as the concentration of an aqueous solution of monoammonium glycyrrhizic acid increases. Furthermore, it was found that a harder gel is formed when the molar ratio between glycyrrhizic acid and local anesthetic having a tertiary amine is 1:2 compared to a case in which the molar ratio is 1:1. It was also found that, when the molar ratio of local anesthetic is increased, the relative amount of an aqueous solution of ropivacaine hydrochloride monohydrate to be added becomes higher, and thus there is a tendency that a softer gel is yielded. The solution amount of the aqueous solution of monoammonium glycyrrhizic acid is preferably used in an amount that is 4 times or higher than the solution amount of the aqueous solution of ropivacaine hydrochloride monohydrate.

Because the gel type local anesthetic agent of the present invention is a gel, it has some fluidity. Thus, it can be administered by any method like spraying, spreading, and injection.

Furthermore, the gel type local anesthetic preparation of the present invention consists of a container and the gel type local anesthetic agent of the present invention encased in the container. As for the container, a glass container and a resin container are preferable, and a container with low water vapor permeability is preferable. Furthermore, it is preferable that the container is provided with an opening and the opening is attached with a detachable sealing member. Furthermore, the gel type local anesthetic preparation is preferably treated by, in a state of being charged in a container, high pressure steam sterilization. Furthermore, as for the shape of the container, a vial container, a syringe, or the like are suitable. As for the syringe, a syringe known in the art can be used. Furthermore, as for the gel type local anesthetic used for the gel type local anesthetic preparation, those of all examples described above can be suitably used.

EXAMPLES

Next, the present invention is explained in detail with reference to the examples. However, the present invention is not limited to those examples and test examples. Furthermore, in the followings, a "solution" means an "aqueous solution", unless particularly described otherwise.

Example 1

About 1000 mg of monoammonium glycyrrhizic acid (molecular weight of 839.96) was weighed, and after adding 20 mL of water, it was heated to 60° C. to prepare a solution of monoammonium glycyrrhizic acid (concentration of monoammonium glycyrrhizic acid: 50 mg/mL). About 590 mg of ropivacaine hydrochloride monohydrate (molecular weight of 328.88, local anesthetic having a secondary amine and a tertiary amine) was weighed precisely, and by dissolving it in 10 mL of water, a solution of ropivacaine hydrochloride (concentration of ropivacaine hydrochloride: 59 mg/mL) was prepared.

15 mL of the above solution of monoammonium glycyrrhizic acid was collected in a screw tube, and by slowly adding 5 mL of a solution of ropivacaine hydrochloride under stirring with a stirrer followed by allowing it to stand for a while, 20 mL of gelated gel type local anesthetic agent of the present invention (Example 1; concentration of monoammonium glycyrrhizic acid: 37.5 mg/mL, concentration of ropivacaine hydrochloride: 14.7 mg/mL, pH 4.58, molar ratio between monoammonium glycyrrhizic acid and ropivacaine hydrochloride: 1:1) was prepared.

In terms of sense of touch, the gel type local anesthetic agent of Example 1 was found to be a gel having hardness at certain level. It was yellow and transparent and did not show any syneresis either immediately after the preparation or after a lapse of 24 hours.

Example 2

About 500 mg of monoammonium glycyrrhizic acid was weighed, and after adding 20 mL of water, it was heated to 60° C. to prepare a solution of monoammonium glycyrrhizic acid (concentration of monoammonium glycyrrhizic acid: 25 mg/mL). About 590 mg of ropivacaine hydrochloride monohydrate was weighed precisely, and by dissolving it in 10 mL of water, a solution of ropivacaine hydrochloride (concentration of ropivacaine hydrochloride: 59 mg/mL) was prepared.

17.2 mL of the above solution of monoammonium glycyrrhizic acid was collected in a screw tube, and by slowly adding 2.8 mL of a solution of ropivacaine hydrochloride under stirring with a stirrer followed by allowing it to stand for a while, 20 mL of gelated gel type local anesthetic agent of the present invention (Example 2; concentration of monoammonium glycyrrhizic acid: 21.5 mg/mL, concentration of ropivacaine hydrochloride: 8.4 mg/mL, pH 3.85, molar ratio between monoammonium glycyrrhizic acid and ropivacaine hydrochloride: 1:1) was prepared.

In terms of sense of touch, the gel type local anesthetic agent of Example 2 was found to be a gel having hardness at certain level. It was yellow and transparent and did not show any syneresis either immediately after the preparation or after a lapse of 24 hours.

Example 3

About 250 mg of monoammonium glycyrrhizic acid was weighed, and after adding 20 mL of water, it was heated to 60° C. to prepare a solution of monoammonium glycyrrhizic acid (concentration of monoammonium glycyrrhizic acid: 12.5 mg/mL).

About 590 mg of ropivacaine hydrochloride monohydrate was weighed precisely, and by dissolving it in 10 mL of water, a solution of ropivacaine hydrochloride (concentration of ropivacaine hydrochloride: 59 mg/mL) was prepared.

18.5 mL of the above solution of monoammonium glycyrrhizic acid was collected in a screw tube, and by slowly adding 1.5 mL of a solution of ropivacaine hydrochloride under stirring with a stirrer followed by allowing it to stand for a while, 20 mL of gelated gel type local anesthetic agent of the present invention (Example 3; concentration of monoammonium glycyrrhizic acid: 11.5 mg/mL, concentration of ropivacaine hydrochloride: 4.5 mg/mL, pH 4.39, molar ratio between monoammonium glycyrrhizic acid and ropivacaine hydrochloride: 1:1) was prepared.

In terms of sense of touch, the gel type local anesthetic agent of Example 3 was found to be a gel having hardness at certain level. It was yellow and transparent and did not show any syneresis either immediately after the preparation or after a lapse of 24 hours.

Example 4

20 mL of the gel type local anesthetic agent was prepared in the same manner as Example 1. The resulting gel type local anesthetic agent was put in a glass container, and after sealing, subjected to high pressure steam sterilization (121° C., for 20 minutes) to prepare 20 mL of sterilized gel type local anesthetic agent of the present invention (Example 4; concentration of monoammonium glycyrrhizic acid: 37.5 mg/mL, concentration of ropivacaine hydrochloride: 14.7 mg/mL).

Example 5

20 mL of the gel type local anesthetic agent was prepared in the same manner as Example 2. The resulting gel type local anesthetic agent was put in a glass container, and after sealing, subjected to high pressure steam sterilization (121° C., for 20 minutes) to prepare 20 mL of sterilized gel type local anesthetic agent of the present invention (Example 5; concentration of monoammonium glycyrrhizic acid: 21.5 mg/mL, concentration of ropivacaine hydrochloride: 8.4 mg/mL).

Example 6

20 mL of the gel type local anesthetic agent was prepared in the same manner as Example 3. The resulting gel type local anesthetic agent was put in a glass container, and after sealing, subjected to high pressure steam sterilization (121° C., for 20 minutes) to prepare 20 mL of sterilized gel type local anesthetic agent of the present invention (Example 6; concentration of monoammonium glycyrrhizic acid: 11.5 mg/mL, concentration of ropivacaine hydrochloride: 4.5 mg/mL).

(Experiment 1) Measurement of Content of Ropivacaine Hydrochloride

The content of ropivacaine hydrochloride was measured for the gel type local anesthetic agent of Examples 1 to 6.

After adding the gel type local anesthetic agent of Examples 1 to 6 to a 1-ml test tube, 5 mL of water was precisely added thereto followed by heating to 60° C. to dissolve the gel. To the dissolved solution, water was additionally added to have 50 mL, and the resulting solution was used as a sample solution. For each sample solution, measurement by HPLC was carried out according to the ropivacaine hydrochloride quantification method, which will be described later. The results are as shown in Table 1.

Quantification of ropivacaine hydrochloride was carried out according to the method described in "Ropivacaine Hydrochloride Injection" <Assay> of USP (United States Pharmacopoeia) Monographs. The content of ropivacaine hydrochloride in the table indicates the measurement amount relative to the addition amount of ropivacaine hydrochloride, in which the content is expressed in %.

TABLE 1

|           | Content of ropivacaine hydrochloride (%) |
|-----------|------------------------------------------|
| Example 1 | 100.96 |
| Example 2 | 103.16 |
| Example 3 | 101.32 |
| Example 4 | 92.84 |
| Example 5 | 102.13 |
| Example 6 | 101.30 |

(Experiment 2) Test for Determining Release of Ropivacaine

For the gel type local anesthetic agent of Examples 1 to 6, the release amount of ropivacaine hydrochloride was measured over time.

One table of PBS (phosphate buffer solution) tablet (manufactured by MP Biomedicals) was added with water to have 100 mL precisely, and thus a phosphate buffer solution was prepared. To 1 mL of the gel type local anesthetic agent, which has been prepared in Examples 1 to 6, 5 mL of the phosphate buffer solution was added to prepare a base sample in a container immersed in an incubator at 37° C. The base sample was collected in an amount of 1 mL precisely at time points of 5 minutes, 10 minutes, 30 minutes, 1 hour, 2 hours, 3 hours, 4 hours, 6 hours, 24 hours, 30 hours, 48 hours, 54 hours, and 72 hours. By adding, to the collected base sample, a mobile phase of HPLC (mixture (3:2) of acetonitrile and 0.02 mol/L phosphate buffer solution of pH 8.0) to have 5 mL precisely, a sample solution was prepared. Furthermore, at the each time point, 1 mL of the same phosphate buffer solution which has been separately prepared (i.e., solution adjusted to 100 mL precisely as obtained by adding water to one tablet of the same PBS tablet as above) was added thereto whenever the 1 mL is collected from the base sample so as to maintain the base sample at the same amount. For the each test solution, measurement by HPLC was carried out according to the ropivacaine hydrochloride quantification method described above. The results are as shown in Table 2 to Table 4.

TABLE 2

| Time | Example 1 Release rate (%) | Example 4 Release rate (%) |
|------|---------------------------|---------------------------|
| 5 Minutes  | 5.76  | —     |
| 10 Minutes | 14.11 | 10.01 |
| 30 Minutes | 19.50 | 18.00 |
| 1          | 28.51 | 24.89 |

TABLE 2-continued

| Time | Example 1 Release rate (%) | Example 4 Release rate (%) |
|---|---|---|
| 2 | 35.96 | 33.50 |
| 3 | 44.52 | — |
| 4 | 45.89 | 45.24 |
| 6 | 51.16 | 50.94 |
| 24 | 68.71 | 57.33 |
| 30 | 74.26 | — |
| 48 | 79.51 | 76.85 |
| 54 | 78.99 | — |
| 72 | 82.80 | 83.39 |

TABLE 3

| Time | Example 2 Release rate (%) | Example 5 Release rate (%) |
|---|---|---|
| 5 Minutes | 7.45 | — |
| 10 Minutes | 17.35 | 10.44 |
| 30 Minutes | 29.52 | 21.74 |
| 1 | 44.65 | 33.02 |
| 2 | 57.84 | 47.62 |
| 3 | 66.83 | — |
| 4 | 64.02 | 60.59 |
| 6 | 71.98 | 67.62 |
| 24 | 87.93 | 74.18 |
| 30 | 89.62 | — |
| 48 | 93.15 | 93.27 |
| 54 | 94.05 | — |
| 72 | 98.95 | 96.00 |

TABLE 4

| Time | Example 3 Release property (%) | Example 6 Release property (%) |
|---|---|---|
| 5 Minutes | 8.65 | — |
| 10 Minutes | 13.32 | 15.98 |
| 30 Minutes | 32.34 | 32.48 |
| 1 | 73.59 | 54.37 |
| 2 | 78.42 | 78.50 |
| 3 | 82.81 | — |
| 4 | 86.92 | 84.56 |
| 6 | 88.36 | 90.52 |
| 24 | 95.81 | 90.94 |
| 30 | 97.01 | — |
| 48 | 96.60 | 97.27 |
| 54 | 96.30 | — |
| 72 | 96.62 | 100.40 |

From the results of Table 2 to Table 4, it was confirmed that any gel type local anesthetic agent of Examples 1 to 6 has a sufficient sustained release property at early application stage, i.e., the release rate after 1 hour was 20% or higher, and it also has a certain long-term sustained release property up to 72 hours. It was also confirmed that the sustained release property of the gel type local anesthetic agent of the present invention is not affected even when the agent is subjected to high pressure steam sterilization.

Example 7

About 50 mg of monoammonium glycyrrhizic acid (manufactured by Maruzen Pharmaceuticals Co., Ltd., molecular weight of 839.96) was weighed, and after adding 10 mL of water, it was heated to 60° C. to prepare a solution of monoammonium glycyrrhizic acid (concentration of monoammonium glycyrrhizic acid: 5 mg/mL).

250 mg of bupivacaine hydrochloride (manufactured by JINAN CHENGHUI-SHUANGDA Chemic Co., Ltd., molecular weight of 342.9, local anesthetic having a secondary amine and a tertiary amine) was weighed precisely, and by dissolving it in 5 mL of water, a solution of bupivacaine hydrochloride (concentration of bupivacaine hydrochloride: 50 mg/mL) was prepared.

1 mL of the above solution of monoammonium glycyrrhizic acid was collected in a screw tube, and by slowly adding 41 µL of a solution of bupivacaine hydrochloride under stirring with a stirrer followed by allowing it to stand for a while, gelated gel type local anesthetic agent of the present invention (Example 7; concentration of monoammonium glycyrrhizic acid: 4.8 mg/mL, concentration of bupivacaine hydrochloride: 2.0 mg/mL, molar ratio between monoammonium glycyrrhizic acid and bupivacaine hydrochloride: 1:1) was prepared.

In terms of sense of touch, the gel type local anesthetic agent of Example 7 was found to be a gel having hardness at certain level. It was yellow and transparent and did not show any syneresis either immediately after the preparation or after a lapse of 24 hours.

Example 8

About 50 mg of monoammonium glycyrrhizic acid (manufactured by Maruzen Pharmaceuticals Co., Ltd., molecular weight of 839.96) was weighed, and after adding 10 mL of water, it was heated to 60° C. to prepare a solution of monoammonium glycyrrhizic acid (concentration of monoammonium glycyrrhizic acid: 5 mg/mL).

250 mg of levobupivacaine hydrochloride (manufactured by JINAN CHENGHUI-SHUANGDA Chemic Co., Ltd., molecular weight of 342.9, local anesthetic having a secondary amine and a tertiary amine) was weighed precisely, and by dissolving it in 5 mL of water, a solution of levobupivacaine hydrochloride (concentration of levobupivacaine hydrochloride: 50 mg/mL) was prepared.

1 mL of the above solution of monoammonium glycyrrhizic acid was collected in a screw tube, and by slowly adding 41 µL of a solution of levobupivacaine hydrochloride under stirring with a stirrer followed by allowing it to stand for a while, a gelated gel type local anesthetic agent of the present invention (Example 8; concentration of monoammonium glycyrrhizic acid: 4.8 mg/mL, concentration of levobupivacaine hydrochloride: 2.0 mg/mL, molar ratio between monoammonium glycyrrhizic acid and levobupivacaine hydrochloride: 1:1) was prepared.

In terms of sense of touch, the gel type local anesthetic agent of Example 8 was found to be a gel having hardness at certain level. It was yellow and transparent and did not show any syneresis either immediately after the preparation or after a lapse of 24 hours.

Example 9

About 50 mg of monoammonium glycyrrhizic acid (manufactured by Maruzen Pharmaceuticals Co., Ltd., molecular weight of 839.96) was weighed, and after adding 10 mL of water, it was heated to 60° C. to prepare a solution of monoammonium glycyrrhizic acid (concentration of monoammonium glycyrrhizic acid: 5 mg/mL).

100 mg of lidocaine hydrochloride (manufactured by Sigma, molecular weight of 288.8, local anesthetic having a secondary amine and a tertiary amine) was weighed precisely, and by dissolving it in 2 mL of water, a solution of lidocaine hydrochloride monohydrate (concentration of lidocaine hydrochloride: 50 mg/mL) was prepared.

1 mL of the above solution of monoammonium glycyrrhizic acid was collected in a screw tube, and by slowly adding 34 µL of a solution of lidocaine hydrochloride under stirring with a stirrer followed by allowing it to stand for a while, a gelated gel type local anesthetic agent of the present invention (Example 9; concentration of monoammonium glycyrrhizic acid: 4.8 mg/mL, concentration of lidocaine hydrochloride: 1.6 mg/mL, molar ratio between monoammonium glycyrrhizic acid and lidocaine hydrochloride: 1:1) was prepared.

In terms of sense of touch, the gel type local anesthetic agent of Example 9 was found to be a gel having hardness at certain level. It was yellow and transparent and did not show any syneresis either immediately after the preparation or after a lapse of 24 hours.

Example 10

About 500 mg of monoammonium glycyrrhizic acid (manufactured by Maruzen Pharmaceuticals Co., Ltd., molecular weight of 839.96) was weighed, and after adding 10 mL of water, it was heated to 60° C. to prepare a solution of monoammonium glycyrrhizic acid (concentration of monoammonium glycyrrhizic acid: 50 mg/mL).

100 mg of procaine hydrochloride (manufactured by Tokyo Chemical Industry Co., Ltd., molecular weight of 236.3, local anesthetic having a primary amine and a tertiary amine) was weighed precisely, and by dissolving it in 2 mL of water, a solution of procaine hydrochloride monohydrate (concentration of procaine hydrochloride: 50 mg/mL) was prepared.

1 mL of the above solution of monoammonium glycyrrhizic acid was collected in a screw tube, and by slowly adding 28 µL of a solution of procaine hydrochloride under stirring with a stirrer followed by allowing it to stand for a while, a gelated gel type local anesthetic agent of the present invention (Example 10; concentration of monoammonium glycyrrhizic acid: 4.9 mg/mL, concentration of procaine hydrochloride: 1.4 mg/mL, molar ratio between monoammonium glycyrrhizic acid and procaine hydrochloride: 1:1) was prepared.

In terms of sense of touch, the gel type local anesthetic agent of Example 10 was found to be a gel having hardness at certain level. It was yellow and transparent and did not show any syneresis either immediately after the preparation or after a lapse of 24 hours.

Example 11

About 125 mg of monoammonium glycyrrhizic acid (manufactured by Maruzen Pharmaceuticals Co., Ltd., molecular weight of 839.96) was weighed, and after adding 10 mL of water, it was heated to 60° C. to prepare a solution of monoammonium glycyrrhizic acid (concentration of monoammonium glycyrrhizic acid: 12.5 mg/mL).

250 mg of bupivacaine hydrochloride (manufactured by JINAN CHENGHUI-SHUANGDA Chemic Co., Ltd., molecular weight of 342.9, local anesthetic having a secondary amine and a tertiary amine) was weighed precisely, and by dissolving it in 5 mL of water, a solution of bupivacaine hydrochloride (concentration of bupivacaine hydrochloride: 50 mg/mL) was prepared.

1 mL of the above solution of monoammonium glycyrrhizic acid was collected in a screw tube, and by slowly adding 102 µL of a solution of bupivacaine hydrochloride under stirring with a stirrer followed by allowing it to stand for a while, a gelated gel type local anesthetic agent of the present invention (Example 11; concentration of monoammonium glycyrrhizic acid: 11.3 mg/mL, concentration of bupivacaine hydrochloride: 4.6 mg/mL, molar ratio between monoammonium glycyrrhizic acid and bupivacaine hydrochloride: 1:1) was prepared.

In terms of sense of touch, the gel type local anesthetic agent of Example 11 was found to be a gel having hardness at certain level. It was yellow and transparent and did not show any syneresis either immediately after the preparation or after a lapse of 24 hours.

Example 12

About 125 mg of monoammonium glycyrrhizic acid (manufactured by Maruzen Pharmaceuticals Co., Ltd., molecular weight of 839.96) was weighed, and after adding 10 mL of water, it was heated to 60° C. to prepare a solution of monoammonium glycyrrhizic acid (concentration of monoammonium glycyrrhizic acid: 12.5 mg/mL).

250 mg of levobupivacaine hydrochloride (manufactured by JINAN CHENGHUI-SHUANGDA Chemic Co., Ltd., molecular weight of 342.9, local anesthetic having a secondary amine and a tertiary amine) was weighed precisely, and by dissolving it in 5 mL of water, a solution of levobupivacaine hydrochloride (concentration of levobupivacaine hydrochloride: 50 mg/mL) was prepared.

1 mL of the above solution of monoammonium glycyrrhizic acid was collected in a screw tube, and by slowly adding 102 µL of a solution of levobupivacaine hydrochloride under stirring with a stirrer followed by allowing it to stand for a while, gelated gel type local anesthetic agent of the present invention (Example 12; concentration of monoammonium glycyrrhizic acid: 11.3 mg/mL, concentration of levobupivacaine hydrochloride: 4.6 mg/mL, molar ratio between monoammonium glycyrrhizic acid and levobupivacaine hydrochloride: 1:1) was prepared.

In terms of sense of touch, the gel type local anesthetic agent of Example 12 was found to be a gel having hardness at certain level. It was yellow and transparent and did not show any syneresis either immediately after the preparation or after a lapse of 24 hours.

Example 13

About 125 mg of monoammonium glycyrrhizic acid (manufactured by Maruzen Pharmaceuticals Co., Ltd., molecular weight of 839.96) was weighed, and after adding 10 mL of water, it was heated to 60° C. to prepare a solution of monoammonium glycyrrhizic acid (concentration of monoammonium glycyrrhizic acid: 12.5 mg/mL).

100 mg of lidocaine hydrochloride (manufactured by Sigma, molecular weight of 288.8, local anesthetic having a secondary amine and a tertiary amine) was weighed precisely, and by dissolving it in 2 mL of water, a solution of lidocaine hydrochloride monohydrate (concentration of lidocaine hydrochloride: 50 mg/mL) was prepared.

1 mL of the above solution of monoammonium glycyrrhizic acid was collected in a screw tube, and by slowly adding 86 µL of a solution of lidocaine hydrochloride under stirring with a stirrer followed by allowing it to stand for a while, a gelated gel type local anesthetic agent of the present invention (Example 13; concentration of monoammonium glycyrrhizic acid: 11.5 mg/mL, concentration of lidocaine hydrochloride: 4.0 mg/mL, molar ratio between monoammonium glycyrrhizic acid and lidocaine hydrochloride: 1:1) was prepared.

In terms of sense of touch, the gel type local anesthetic agent of Example 13 was found to be a gel having hardness at certain level. It was yellow and transparent and did not show any syneresis either immediately after the preparation or after a lapse of 24 hours.

Example 14

About 50 mg of monoammonium glycyrrhizic acid (manufactured by Maruzen Pharmaceuticals Co., Ltd., molecular weight of 839.96) was weighed, and after adding 10 mL of water, it was heated to 60° C. to prepare a solution of monoammonium glycyrrhizic acid (concentration of monoammonium glycyrrhizic acid: 5 mg/mL).

100 mg of procaine hydrochloride (manufactured by Tokyo Chemical Industry Co., Ltd., molecular weight of 236.3, local anesthetic having a primary amine and a tertiary amine) was weighed precisely, and by dissolving it in 2 mL of water, a solution of procaine hydrochloride monohydrate (concentration of procaine hydrochloride: 50 mg/mL) was prepared.

1 mL of the above solution of monoammonium glycyrrhizic acid was collected in a screw tube, and by slowly adding 70 μL of a solution of procaine hydrochloride under stirring with a stirrer followed by allowing it to stand for a while, a gelated gel type local anesthetic agent of the present invention (Example 14; concentration of monoammonium glycyrrhizic acid: 11.7 mg/mL, concentration of procaine hydrochloride: 3.3 mg/mL, molar ratio between monoammonium glycyrrhizic acid and procaine hydrochloride: 1:1) was prepared.

In terms of sense of touch, the gel type local anesthetic agent of Example 14 was found to be a gel having hardness at certain level. It was yellow and transparent and did not show any syneresis either immediately after the preparation or after a lapse of 24 hours.

Example 15

About 250 mg of monoammonium glycyrrhizic acid (manufactured by Maruzen Pharmaceuticals Co., Ltd., molecular weight of 839.96) was weighed, and after adding 10 mL of water, it was heated to 60° C. to prepare a solution of monoammonium glycyrrhizic acid (concentration of monoammonium glycyrrhizic acid: 25 mg/mL).

100 mg of lidocaine hydrochloride (manufactured by Sigma, molecular weight of 288.8, local anesthetic having a secondary amine and a tertiary amine) was weighed precisely, and by dissolving it in 2 mL of water, a solution of lidocaine hydrochloride monohydrate (concentration of lidocaine hydrochloride: 50 mg/mL) was prepared.

1 mL of the above solution of monoammonium glycyrrhizic acid was collected in a screw tube, and by slowly adding 172 μL of a solution of lidocaine hydrochloride under stirring with a stirrer followed by allowing it to stand for a while, a gelated gel type local anesthetic agent of the present invention (Example 15; concentration of monoammonium glycyrrhizic acid: 21.3 mg/mL, concentration of lidocaine hydrochloride: 7.3 mg/mL, molar ratio between monoammonium glycyrrhizic acid and lidocaine hydrochloride: 1:1) was prepared.

In terms of sense of touch, the gel type local anesthetic agent of Example 15 was found to be a gel having hardness at certain level. It was yellow and transparent and did not show any syneresis either immediately after the preparation or after a lapse of 24 hours.

Example 16

About 250 mg of monoammonium glycyrrhizic acid (manufactured by Maruzen Pharmaceuticals Co., Ltd., molecular weight of 839.96) was weighed, and after adding 10 mL of water, it was heated to 60° C. to prepare a solution of monoammonium glycyrrhizic acid (concentration of monoammonium glycyrrhizic acid: 25 mg/mL).

100 mg of procaine hydrochloride (manufactured by Tokyo Chemical Industry Co., Ltd., molecular weight of 236.3, local anesthetic having a primary amine and a tertiary amine) was weighed precisely, and by dissolving it in 2 mL of water, a solution of procaine hydrochloride monohydrate (concentration of procaine hydrochloride: 50 mg/mL) was prepared.

1 mL of the above solution of monoammonium glycyrrhizic acid was collected in a screw tube, and by slowly adding 141 μL of a solution of procaine hydrochloride under stirring with a stirrer followed by allowing it to stand for a while, a gelated gel type local anesthetic agent of the present invention (Example 16; concentration of monoammonium glycyrrhizic acid: 21.9 mg/mL, concentration of procaine hydrochloride: 6.2 mg/mL, molar ratio between monoammonium glycyrrhizic acid and procaine hydrochloride: 1:1) was prepared.

In terms of sense of touch, the gel type local anesthetic agent of Example 16 was found to be a gel having hardness at certain level. It was yellow and transparent and did not show any syneresis either immediately after the preparation or after a lapse of 24 hours.

Example 17

About 500 mg of monoammonium glycyrrhizic acid (manufactured by Maruzen Pharmaceuticals Co., Ltd., molecular weight of 839.96) was weighed, and after adding 10 mL of water, it was heated to 60° C. to prepare a solution of monoammonium glycyrrhizic acid (concentration of monoammonium glycyrrhizic acid: 50 mg/mL).

100 mg of lidocaine hydrochloride (manufactured by Sigma, molecular weight of 288.8, local anesthetic having a secondary amine and a tertiary amine) was weighed precisely, and by dissolving it in 2 mL of water, a solution of lidocaine hydrochloride monohydrate (concentration of lidocaine hydrochloride: 50 mg/mL) was prepared.

1 mL of the above solution of monoammonium glycyrrhizic acid was collected in a screw tube, and by slowly adding 344 μL of a solution of lidocaine hydrochloride under stirring with a stirrer followed by allowing it to stand for a while, a gelated gel type local anesthetic agent of the present invention (Example 17; concentration of monoammonium glycyrrhizic acid: 37.2 mg/mL, concentration of lidocaine hydrochloride: 12.8 mg/mL, molar ratio between monoammonium glycyrrhizic acid and lidocaine hydrochloride: 1:1) was prepared.

In terms of sense of touch, the gel type local anesthetic agent of Example 17 was found to be a gel having hardness at certain level. It was yellow and transparent and did not show any syneresis either immediately after the preparation or after a lapse of 24 hours.

Example 18

About 500 mg of monoammonium glycyrrhizic acid (manufactured by Maruzen Pharmaceuticals Co., Ltd., molecular weight of 839.96) was weighed, and after adding 10 mL of water, it was heated to 60° C. to prepare a solution of monoammonium glycyrrhizic acid (concentration of monoammonium glycyrrhizic acid: 50 mg/mL).

100 mg of procaine hydrochloride (manufactured by Tokyo Chemical Industry Co., Ltd., molecular weight of 236.3, local anesthetic having a primary amine and a tertiary amine) was weighed precisely, and by dissolving it in 2 mL of water, a solution of procaine hydrochloride monohydrate (concentration of procaine hydrochloride: 50 mg/mL) was prepared.

1 mL of the above solution of monoammonium glycyrrhizic acid was collected in a screw tube, and by slowly adding 281 µL of a solution of procaine hydrochloride under stirring with a stirrer followed by allowing it to stand for a while, a gelated gel type local anesthetic agent of the present invention (Example 18; concentration of monoammonium glycyrrhizic acid: 39.0 mg/mL, concentration of procaine hydrochloride: 11.0 mg/mL, molar ratio between monoammonium glycyrrhizic acid and procaine hydrochloride: 1:1) was prepared.

In terms of sense of touch, the gel type local anesthetic agent of Example 18 was found to be a gel having hardness at certain level. It was yellow and transparent and did not show any syneresis either immediately after the preparation or after a lapse of 24 hours.

INDUSTRIAL APPLICABILITY

The gel type local anesthetic agent of the present invention is as described below.
(1) A gel type local anesthetic agent consisting of a local anesthetic having a tertiary amine and glycyrrhizic acid in which the local anesthetic and glycyrrhizic acid are gelated to form a gel.

Accordingly, when the agent is spread or sprayed on a surgery area inside a cutting part and the cutting part is sutured, although gel degradation is under progress, the local anesthetic remains on an administration site for a certain long period of time until to have degradation of the whole amount because the agent has been gelated. Accordingly, effective alleviation of pains is achieved. Furthermore, as glycyrrhizic acid is also released into a subject in accordance with degradation of a gel, it is expected to have an anti-inflammatory activity of glycyrrhizic acid. Furthermore, it is expected for this local anesthetic agent to exhibit a stable sustained release property even after high pressure steam sterilization.

Furthermore, the above embodiment can be also as described below.
(2) The gel type local anesthetic agent described in above (1) in which the local anesthetic is an amide type local anesthetic or an ester type local anesthetic.
(3) The gel type local anesthetic agent described in above (1) or (2) in which the amine of the local anesthetic is derived from a piperidine skeleton.
(4) The gel type local anesthetic agent described in any one of above (1) to (3) in which the local anesthetic has both a secondary amine and a tertiary amine.
(5) The gel type local anesthetic agent described in above (1) in which the local anesthetic is at least one selected from the group consisting of ropivacaine, bupivacaine, levobupivacaine, lidocaine, procaine, tetracaine, cocaine, benzocaine, mepivacaine, prilocaine, dibucaine, and chloroprocaine.
(6) The gel type local anesthetic agent described in any one of above (1) to (5) in which the local anesthetic agent has pH of 6 or less.
(7) The gel type local anesthetic agent described in any one of above (1) to (6) in which a release rate of the local anesthetic by the local anesthetic agent is 20% or higher 1 hour after the administration and a release rate of the local anesthetic by the local anesthetic agent is 80% or lower 6 hours after the administration.
(8) The gel type local anesthetic agent described in any one of above (1) to (7) in which the gel type local anesthetic agent has been treated with high pressure steam sterilization.
(9) The gel type local anesthetic agent described in any one of above (1) to (8) in which molar ratio between the glycyrrhizic acid and local anesthetic in the gel type local anesthetic agent is 1:0.5 to 1:10.

Furthermore, the gel type local anesthetic preparation of the present invention is as described below.
(10) A gel type local anesthetic preparation consisting of a container and the gel type local anesthetic agent described in any one of above (1) to (9) that is filled in the container.

Furthermore, the above embodiment can be also as described below.
(11) The gel type local anesthetic preparation of above (10) in which the container is a syringe.

The invention claimed is:
1. A gel type local anesthetic agent comprising a complex and water,
wherein the complex is made by a glycyrrhizic acid and a local anesthetic,
the local anesthetic has both of a secondary amine and a tertiary amine or both of a primary amine and a tertiary amine and can be prepared as an aqueous solution of the local anesthetic,
the glycyrrhizic acid is a water soluble salt of glycyrrhizic acid,
the complex is formed by an interaction between carboxy group of the water soluble salt of glycyrrhizic acid and the amine of the local anesthetics,
the local anesthetic agent has a gel state formed only by the complex and water,
the local anesthetic agent does not contain a compound for gelation other than the water soluble salt of glycyrrhizic acid and the local anesthetic, and
a molar ratio between the water soluble salt of glycyrrhizic acid and the local anesthetic in the local anesthetic agent is in a range of 1:0.5 to 1:10.
2. The gel type local anesthetic agent according to claim 1, wherein the amine of the local anesthetic is derived from a piperidine skeleton.
3. The gel type local anesthetic agent according to claim 1, wherein the local anesthetic has both a secondary amine and a tertiary amine.
4. The gel type local anesthetic agent according to claim 1, wherein the local anesthetic is at least one selected from the group consisting of ropivacaine, bupivacaine, levobupivacaine, lidocaine, procaine, tetracaine, mepivacaine, dibucaine, and chloroprocaine.
5. The gel type local anesthetic agent according to claim 1, wherein the local anesthetic agent has pH of 6 or less.
6. The gel type local anesthetic agent according to claim 1, wherein a release rate of the local anesthetic by the local anesthetic agent is 20% or higher 1 hour after the administration and a release rate of the local anesthetic by the local anesthetic is 80% or lower 6 hours after the administration.
7. The gel type local anesthetic agent according to claim 1, wherein the gel type local anesthetic agent has been treated with high pressure steam sterilization.
8. The gel type local anesthetic agent according to claim 1, wherein the local anesthetic has both of a primary amine and a tertiary amine.

9. The gel type local anesthetic agent according to claim 1, wherein the molar ratio between the glycyrrhizic acid and local anesthetic in the gel type local anesthetic agent is in a range of 1:1 to 1:3.

10. The gel type local anesthetic agent according to claim 1, wherein said local anesthetic is ropivacaine hydrochloride, bupivacaine hydrochloride, levobupivacaine hydrochloride, lidocaine hydrochloride, or procaine hydrochloride.

11. A composition comprising a container and the gel type local anesthetic agent according to claim 1 that is filled in the container.

12. The composition according to claim 11, wherein the container is a syringe.

13. A local anesthetic agent consisting of
water, glycyrrhizic acid and a local anesthetic,
wherein the local anesthetic has both of a secondary amine and a tertiary amine or both of a primary amine and a tertiary amine and can be prepared as an aqueous solution of the local anesthetic,
the glycyrrhizic acid is a water soluble salt of glycyrrhizic acid,
the local anesthetic agent includes a complex formed by a interaction between carboxy group of the water soluble salt of glycyrrhizic acid and the amine of the local anesthetics,
the local anesthetic agent has a gel state formed by the complex and water.

14. An anesthetic gel formulation comprising
a gel matrix comprising a water soluble salt of glycyrrhizic acid and a local anesthetic comprising both of a secondary amine and a tertiary amine or both of a primary amine and a tertiary amine;
wherein the anesthetic gel formulation does not contain a compound for gelation other than the water soluble salt of glycyrrhizic acid and the local anesthetic.

15. The anesthetic gel formulation of claim 14, wherein the molar ratio between the glycyrrhizic acid and local anesthetic in the gel type local anesthetic agent is in a range of 1:0.5 to 1:10.

16. The anesthetic gel formulation of claim 14 further comprising water.

17. The anesthetic gel formulation of claim 14, wherein the amine of the local anesthetic is derived from a piperidine skeleton.

18. The anesthetic gel formulation of claim 14, wherein the local anesthetic has both a secondary amine and a tertiary amine.

19. The anesthetic gel formulation of claim 14, wherein the local anesthetic comprises at least one of the compounds selected from the group consisting of ropivacaine, bupivacaine, levobupivacaine, lidocaine, procaine, tetracaine, mepivacaine, dibucaine, and chloroprocaine.

20. The anesthetic gel formulation of claim 14, wherein the anesthetic gel formulation has pH of 6 or less.

21. The anesthetic gel formulation of claim 14, wherein the anesthetic gel formulation possesses a release rate of the local anesthetic of 20% or higher 1 hour after the administration and 80% or lower 6 hours after the administration.

22. The anesthetic gel formulation of claim 14, wherein said local anesthetic is ropivacaine hydrochloride, bupivacaine hydrochloride, levobupivacaine hydrochloride, lidocaine hydrochloride, or procaine hydrochloride.

* * * * *